US00PP25557P2

(12) United States Plant Patent
Jamieson

(10) Patent No.: US PP25,557 P2
(45) Date of Patent: May 12, 2015

(54) *AGAPANTHUS* PLANT NAMED 'JONIE'

(50) Latin Name: *Agapanthus praecox*
Varietal Denomination: Jonie

(71) Applicant: Richard Jamieson, Kirstenhof (ZA)

(72) Inventor: Richard Jamieson, Kirstenhof (ZA)

(73) Assignee: The Pink Geranium Nursery, Elsenburg (ZA)

( * ) Notice: Subject to any disclaimer, the term of this patent is extended or adjusted under 35 U.S.C. 154(b) by 13 days.

(21) Appl. No.: 13/998,170

(22) Filed: Oct. 8, 2013

(51) Int. Cl.
*A01H 5/02* (2006.01)

(52) U.S. Cl.
USPC ..... Plt./398

(58) Field of Classification Search
CPC ..... A01H 5/02; A01H 5/00
USPC ..... Plt./398
See application file for complete search history.

*Primary Examiner* — Kent L Bell
(74) *Attorney, Agent, or Firm* — Penny J. Aguirre

(57) ABSTRACT

A new cultivar of *Agapanthus* named 'Jonie', characterized by its mid season blooming habit, its blue-purple flowers that are held semi pendulous from pedicel, its medium sized, compact flower heads, and its short flowering stems.

2 Drawing Sheets

Botanical classification: *Agapanthus praecox.*
Varietal denomination: 'Jonie'.

BACKGROUND OF THE INVENTION

The present invention relates to a new and distinct cultivar of *Agapanthus praecox* and will be referred to hereafter by its cultivar name, 'Jonie'. 'Jonie' represents a new perennial herb grown for landscape and container use.

The new *Agapanthus* originated as the result of an on going breeding program in Cape Town, Republic of South Africa. The goal of the breeding program was to produce a cultivar of *Agapanthus* with unique characteristics and a compact plant habit useful for container use.

'Jonie' originated as a seedling that arose from seed planted from open pollination of an unnamed plant of *Agapanthus praecox* from the Inventor's breeding program in 2002. The male parent is unknown. The new *Agapanthus* was selected as a single unique plant in December of 2004.

Asexual propagation of the new cultivar was first accomplished by in vitro propagation under the direction of the Inventor in December of 2005 in Cape Town, Republic of South Africa. Asexual propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Jonie' as a distinct cultivar of *Agapanthus.*

1. 'Jonie' exhibits a mid season blooming habit.
2. 'Jonie' exhibits blue-purple flowers that are held semi pendulous from pedicel.
3. 'Jonie' exhibits medium sized, compact flower heads.
4. 'Jonie' exhibits short flowering stems.

The female parent differs from 'Jonie' in having a taller plant height and flower heads that are less compact. 'Jonie' can be compared to the cultivars 'Peter Pan' (not patented) and 'Snowball' (not patented). 'Peter Pan' is similar to 'Jonie' in being evergreen, in having blue flowers, and a short plant height. 'Peter Pan' differs from 'Jonie' in having lighter colored flowers that are held more outward on less compact flower heads. 'Snowball' is similar to 'Jonie' in being evergreen, in having full flower heads, and in having short flowering stems. 'Snowball' differs from 'Jonie' in having white flowers with less pendulous flowers.

BRIEF DESCRIPTION OF THE DRAWINGS

The accompanying colored photographs illustrate the overall appearance and distinct characteristics of the new *Agapanthus*. The photographs were taken of a one year-old plant of 'Jonie' as field grown outdoors in Cape Town, Republic of South Africa.

The photograph in FIG. 1 provides a close-up view of an inflorescence of 'Jonie'.

Figure 1:
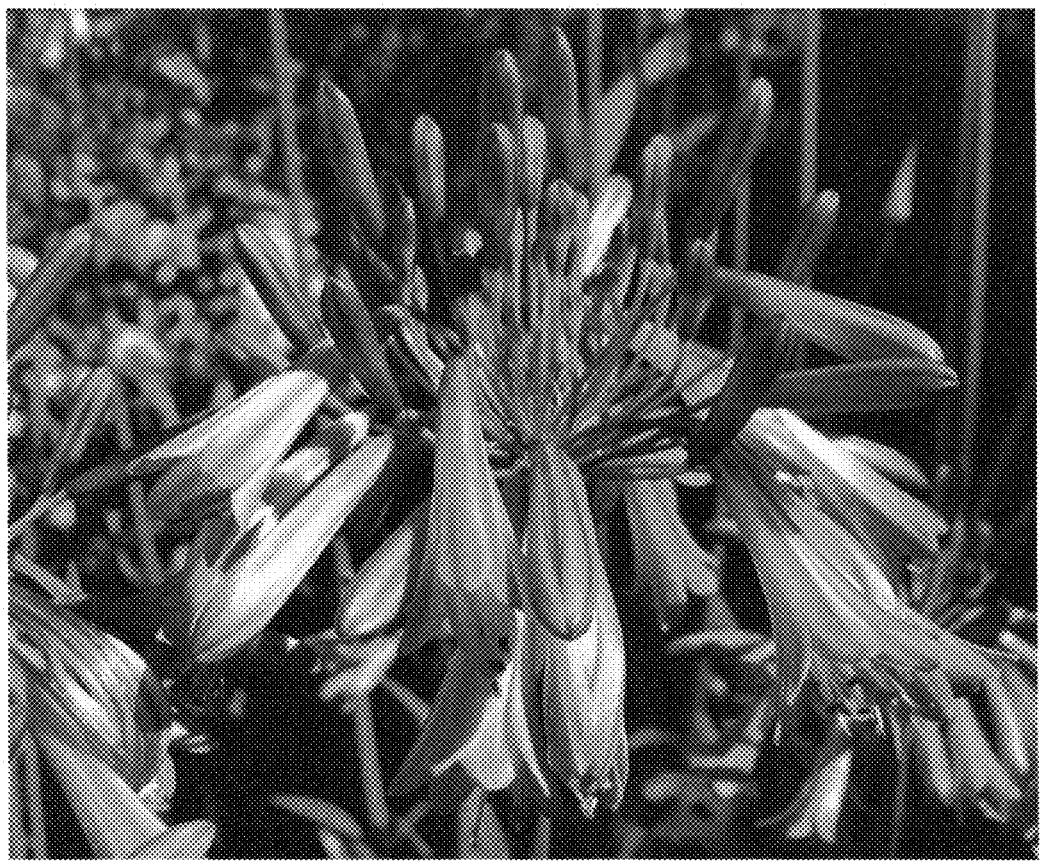
Figure 2:
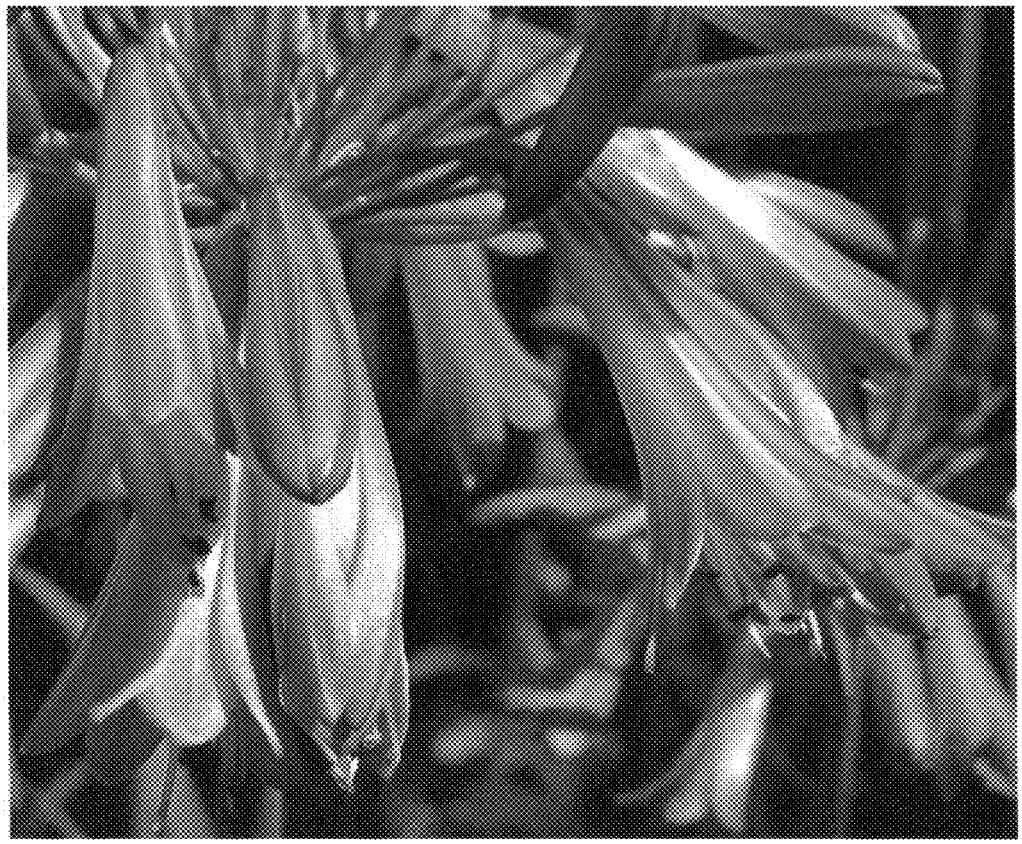

The photograph in FIG. 2 provides a close-up view of the flowers of 'Jonie'.

The colors in the photographs are as close as possible with the photographic and printing technology utilized and color values cited in the detailed botanical description accurately describe the colors of the new *Agapanthus.*

DETAILED BOTANICAL DESCRIPTION

The general observations and descriptions describe plants about two years-old in age as grown outdoors under field conditions in Cape Town, Republic of South Africa. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—4 to 6 weeks in mid summer in Cape Town, Republic of South Africa.

*Plant type.*—Evergreen perennial herb.

*Plant habit.*—Upright with cascading foliage.

*Height and spread.*—Reaches a height of about 50 cm in bloom with and a spread of about 50 cm.

*Cold hardiness.*—At least to U.S.D.A. Zone 8.

*Diseases and pests.*—No susceptibility or resistance to diseases or pests has been observed.

*Root description.*—Fleshy main roots and fibrous secondary roots.

*Propagation.*—Tissue culture and division.

*Root development.*—A division will root and finish in a 6-inch container in about 90 days at 25° C. with high light intensity.

*Growth rate.*—Moderate.

Foliage description:

*Leaf shape.*—Linear.

*Leaf division.*—Simple.

*Leaf base.*—Cuneate.

*Leaf arrangement.*—2-ranked, in rosette.

*Leaf apex.*—Acute.

*Leaf aspect.*—Emerging leaves erect, then cascade.

*Leaf venation.*—Parallel, color matches leaf coloration.

*Leaf margins.*—Entire.

*Leaf size.*—Average of 30 cm in length and 1.5 cm in width.

*Leaf surface.*—Glabrous, slightly glossy.

*Leaf substance.*—Thick and leathery, moderate to high durability to stress.

*Leaf number.*—Average of 6 per rosette.

*Leaf color.*—Young leaves, upper and lower surface; a blend 137B and 137C, mature leaves, upper and lower surface surface; N137A and a blend of 144B and 144D near base.

*Leaf attachment.*—Sessile to crown.

Flower description:

*Inflorescence type.*—Simple umbel.

*Flower fragrance.*—None.

*Flower type.*—Narrow campanulate.

*Flower number.*—Full flower heads; an average of about 45 flowers per umbel, one umbel per peduncle and one peduncle per rosette.

*Inflorescence size.*—Average of 4.5 cm in depth and 8.5 cm in diameter.

*Flower size.*—About 3 cm in depth and 1.8 cm in width.

*Lastingness of inflorescence.*—About 10 days.

*Flower aspect.*—Held semi pendulous from pedicel.

*Peduncle.*—Strong, round in shape with one side slightly flattened, held erect, average of 25 cm in length and 1 cm in width at distal region and 6 mm in width at proximal region, surface is glabrous, color a blend of 137A and 144A.

*Pedicels.*—Strong, average of 8 mm in length and 1.5 mm in width, held erect to outward, color 144A, surface is glabrous.

*Flower buds.*—Elliptic-obovate in shape, average of 2.3 cm in length and 5 mm in width, color a blend of 96B and 145D and suffused with 96B More prevalent towards apex.

*Tepals.*—6, narrow obovate in shape, entire margin, glabrous on inner and outer surface, acute apex with a small tuft of hair; N155A in color at very tip, base is fused to base of stamens, average of 2.6 cm in length and 5 mm in width, color when opening and mature inner surface; 97D with center stripe and margins 94A, color when opening and mature outer surface; 94C with center stripe and margins 94B.

Reproductive organs:

*Gynoecium.*—1 pistil, average of 8 mm in length, stigma is narrow clavate in shape and a blend of 94B and 94C in color, style is twisted, about 7 mm in length and a blend of N155A and 97D in color, ovary is oval in shape, about 5 mm in length and 3 mm in width, and 145B in color.

*Androcoecium.*—6 stamens, anthers are dorsified, oblong in shape, average of 1.5 mm in length, and 202A in color, filament is 2.1 cm in length and adhered to tepals at base, pollen is moderate in quantity and 11B in color.

*Fruit/seed.*—Have not been observed.

It is claimed:

1. A new and distinct cultivar of *Agapanthus* plant named 'Jonie' as herein illustrated and described.

* * * * *